(12) United States Patent
Kocher

(10) Patent No.: US 10,806,198 B1
(45) Date of Patent: Oct. 20, 2020

(54) PUBLIC HAND PROTECTION SYSTEM (PHPS)

(71) Applicant: Robert William Kocher, McLean, VA (US)

(72) Inventor: Robert William Kocher, McLean, VA (US)

( * ) Notice: Subject to any disclaimer, the term of this patent is extended or adjusted under 35 U.S.C. 154(b) by 0 days.

(21) Appl. No.: 16/809,709

(22) Filed: Mar. 5, 2020

(51) Int. Cl.
*A41D 19/015* (2006.01)
*A41D 1/00* (2018.01)

(52) U.S. Cl.
CPC ....... *A41D 19/01594* (2013.01); *A41D 1/002* (2013.01)

(58) Field of Classification Search
CPC . A47L 25/04; A45F 5/04; A45F 5/004; A41D 19/01594
USPC .................................................. 224/932, 162
See application file for complete search history.

(56) References Cited

U.S. PATENT DOCUMENTS

| | | | | |
|---|---|---|---|---|
| 2,754,532 | A * | 7/1956 | Kanehl | A41B 15/00 15/209.1 |
| 8,276,235 | B2 * | 10/2012 | Naughton | A45F 5/02 15/118 |
| 9,955,776 | B2 * | 5/2018 | Terry | A45F 5/004 |
| 2002/0000455 | A1 * | 1/2002 | Condliff | A45F 5/004 224/162 |
| 2012/0151649 | A1 * | 6/2012 | Peterson | B32B 1/08 2/69 |
| 2012/0187150 | A1 * | 7/2012 | Glasmann | A45F 5/02 222/175 |
| 2013/0125307 | A1 * | 5/2013 | Margalit | A47K 10/02 5/417 |
| 2013/0161363 | A1 * | 6/2013 | Johnson | A45F 5/004 224/162 |

FOREIGN PATENT DOCUMENTS

DE       102011101311 A1 * 11/2012   ......... A41D 19/0041

* cited by examiner

*Primary Examiner* — Scott T McNurlen

(57) ABSTRACT

A system for mitigating the transmission of infectious threats by providing an easy access to a cloth or mitt attached to a retractable cord to allow the user to grab a doorknob, subway passenger strap or pole without having skin contact with public touched surfaces. A protection cloth and retraction cord are attached to a personal attachment device, which can be worn on a belt, also has a container with sanitation solution that is applied to the protection cloth after use and can also be applied to a person's hands. A second cloth is also used to wipe down surfaces such as seats, knobs, switches, etc. providing a reusable sanitation cloth and refillable sanitation container. The invention will reduce the contact transmission of infectious disease threats in a more convenient method than current traditional methods of disposable cloths or liquids.

5 Claims, 6 Drawing Sheets

PUBLIC HAND PROTECTION SYSTEM (PHPS)

CROSS-REFERENCE TO RELATED APPLICATION

None.

FEDERALLY SPONSORED RESEARCH

None

BACKGROUND OF THE INVENTION

Related Art (1) Current State of the Art and Problems to be Overcome

Travel has increased dramatically over the recent years. Local travel, regional travel and international travel have resulted in more and more contact with persons and have greatly increased the potential transmission of infectious diseases through contact. The most common transmission is from contact with an infected person or touching a surface that an infectious person has touched. These surfaces can be door handles, railings, pens, tabletops, airline seats, taxi seats, etc.

Infection normally occurs once a person touches a common surface then touches their face or mouth. Hand washing is typically a good method of protection, but public bathrooms normally require opening or closing doors. Using a disposable hand towel is another good method of avoiding transmission, but soon afterwards there are chances of touching new surfaces and re-washing is perhaps not possible or not reasonable under the circumstances. Using hand sanitizing solutions is another good approach that can be effective against bacterial threats, but may not be as effective against viruses, including viruses that may have been developed in a laboratory. In addition, the constant use of hand sanitizing solution may lead to skin irritation or may provide the user with a false sense of protection. Another disadvantage of using a hand sanitizing solution is the constant use of two hands to open a bottle, pour contents of the bottle onto one hand, sanitize both hands, then reseal the bottle and put the bottle in your pocket, briefcase, or purse, etc.

(2) Advantages of the Current Invention

Some advantages of the Public Hand Protection System (PHPS) of the current invention offers the user a faster, simpler, and readily reusable system. The PHPS can be relatively concealable and easy, with one hand, to pull the protective cloth over the user's hand prior to touching the contact surface. PHPS prevents skin contact with the contaminated surface. The protective cloth can be sanitized after numerous uses by applying the system's sanitizing solution to the protective cloth. Since the sanitizing solution container is attached to the PHPS base plate or attachment system, a person using the invention does not have to put a bottle of sanitization solution in their pocket, purse, etc. The PHPS is self-contained, easy to use and easy to wear.

SUMMARY OF THE EXEMPLARY EMBODIMENTS

The Public Hand Protection System (PHPS) is a system for mitigating transmission of infectious disease threats commonly found on door handles, elevator buttons, subway car passenger straps, passenger poles, and/or other publicly touched surfaces. This system consists of an attachment device that can be mounted to a person; an automatic cord pull-out and retracting system mounted on said attachment device; a contact protection cloth attached to said automatic cord pull-out and retracting system; and, a container of sanitary solution that can dispense a sanitary solution onto said contact protection cloth. Since the system contains a sanitation solution, if there is an infectious disease threat on a door handle, for example, the protection cloth with the sanitation solution on it may reduce or eliminate the threat of infectious disease when someone uses PHPS on a common surface. Potentially, this may reduce the threat to the person or persons following the PHPS user.

REFERENCE NUMERALS FOUND IN THE DRAWINGS

Figure 1:
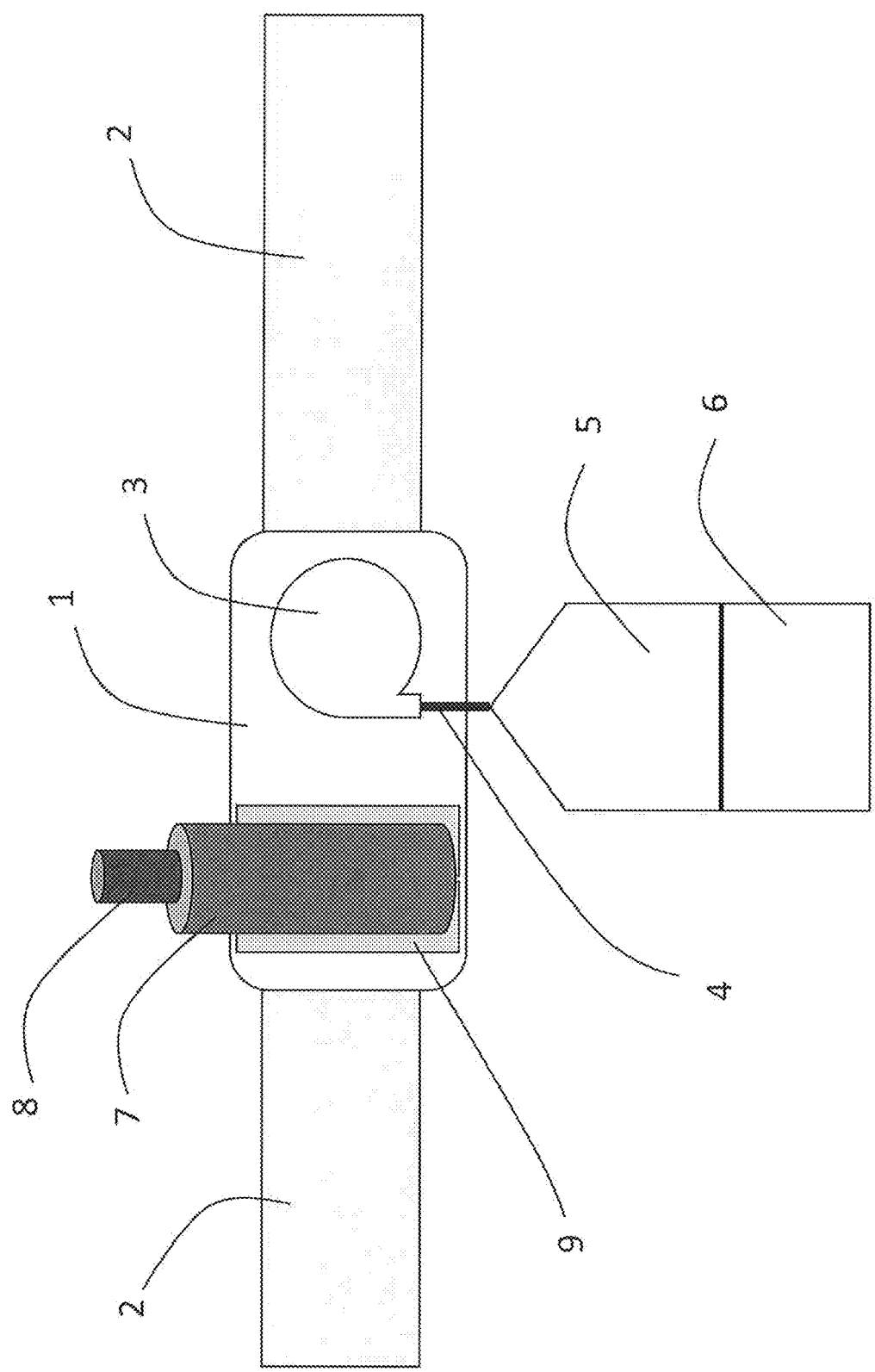
FIG. 1 depicts the primary system mounted on a belt.
Figure 2:
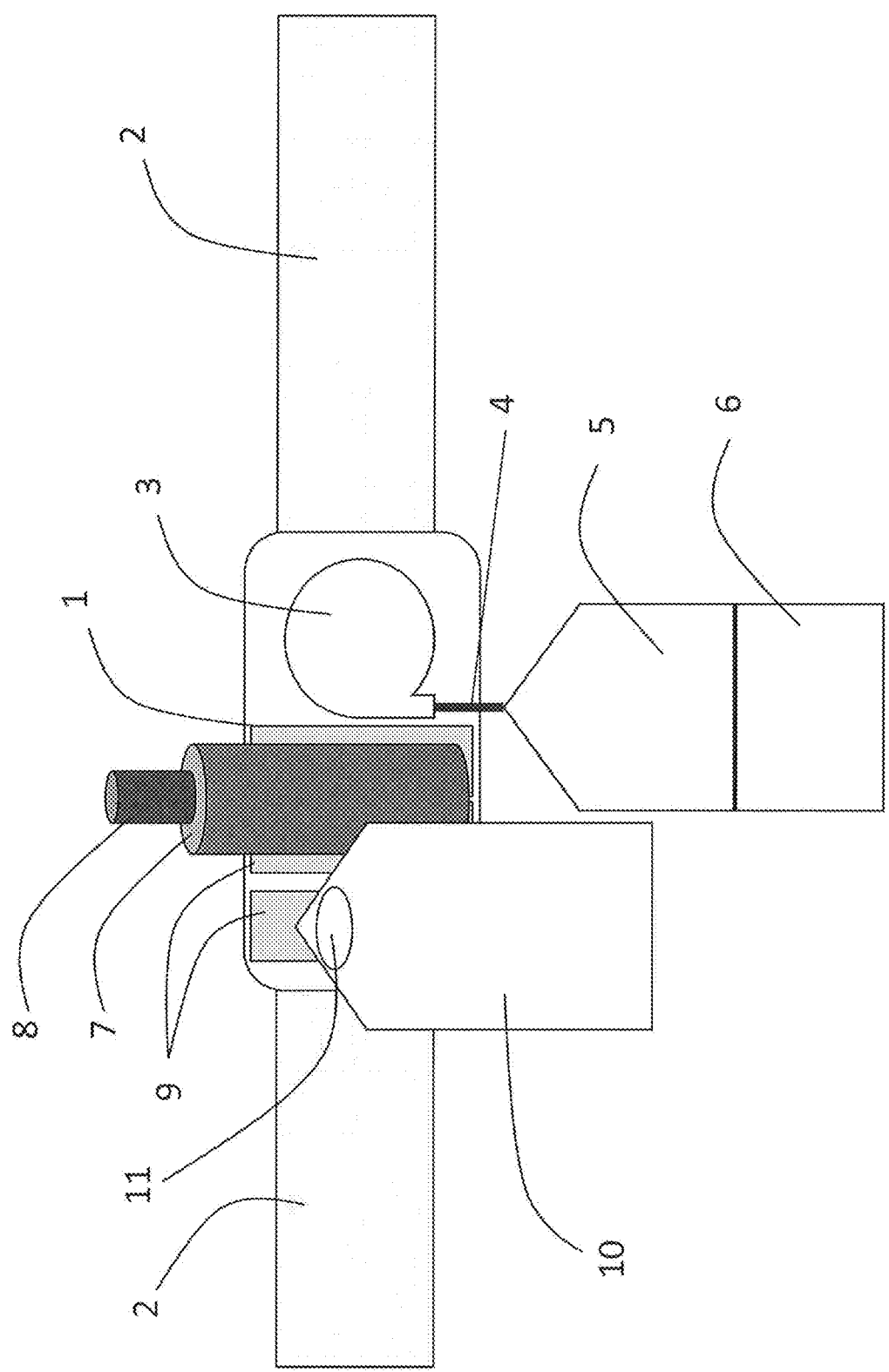
FIG. 2 depicts the addition of a detachable cloth to the base system.

Element 1 is the mounting base for the other elements

Element 2 is a waist belt

Element 3 is a retractable cord housing, mechanism, and attachment device to cloth Element 4 is the retractable cord Element 5 is protective cloth Element 6 is a hand opening on the protective cloth forming a mitt-like cloth Element 7 is a bottle that can hold sanitizing solution Element 8 is the cap or dispensing pump for the sanitizing solution in Element 7

Element 9 is hook-and-loop attachment to hold Element 7 to Element 1

Element 10 is a detachable protective cloth

Element 11 is hook-and-loop attaching Element 10 to Element 1

Element 12 is a belt attachment loop

Element 13 is a belt attachment clip

Element 14 is a neck attachment cord

Element 15 is a door

Element 16 is an individual or user

Element 17 is a door handle

DETAILED DESCRIPTION OF THE EXEMPLARY EMBODIMENTS

The PHPS is a simple-to-use invention that mounts on a user's belt. The system includes a base plate 1, a retractable cord system 3 mounted on the base plate, the cord 4 attached to a protective cloth 5. The protective cloth 5 has a flap 6 forming a mitt-like structure. The flap 6 can be on both sides of the protective cloth 5 to make it easier for the user to find the pocket. A Radio Frequency Identification (RFID) fob, device, or card can also be attached to the cord 4 or cloth 5 to serve as a convenience to the user when approaching an access reader prior to opening a door. Also attached to the mounting base 1 is a bottle 7 that holds a sanitizing solution and dispenses sanitizing solution through the cap 8. The bottle 7 is attached to the mounting base 1 through the use of an attachment system, such as hook-and-loop 9.

In operation, as a user 16 approaches a door handle 17 (FIGS. 6 and 7), the user 16 simply slides his hand down to the protective cloth 5 and into the opening or fold 6. The user 16 then brings his hand up extending the retractable cord 4 until the user touches the door handle 17. The user's hand is protected by the protective cloth making contact with the door handle, thus allowing the user 16 to open the door 17 without any contact between the user 16's hand contacting the doorknob 17. The user 16 then releases the protective cloth 5. At this time, the retraction device 3 retracts the protective cloth 5 to the mounting base 1 on the user's belt 2. The user can also remove the bottle 7 and spray the cloth 5 with sanitizing solution and/or spray the door handle with the solution. A similar approach can be used for elevator buttons or to standing passenger poles on a subway or bus, etc.

Exemplary Embodiment 2 has the addition of a removable cloth 10 that is attached to the mounting base 1 with an attachment mechanism such as hook-and-loop 9. This protective cloth 10 may also or alternatively have an attachment mechanism, such as hook-and-loop 1. This protective cloth 10 is used to protect the user's hand at a greater distance than the retractable cord 4. An example would be on a metro car or bus where a standing passenger holds onto a strap. The protective cloth would be on the strap protecting the user's hand. Thus, in a situation where the extendable cord 4 is unable to extend to a needed distance, the detachable cloth 10 can be used instead of the mitt attached to the extendable cord.

Figure 3:
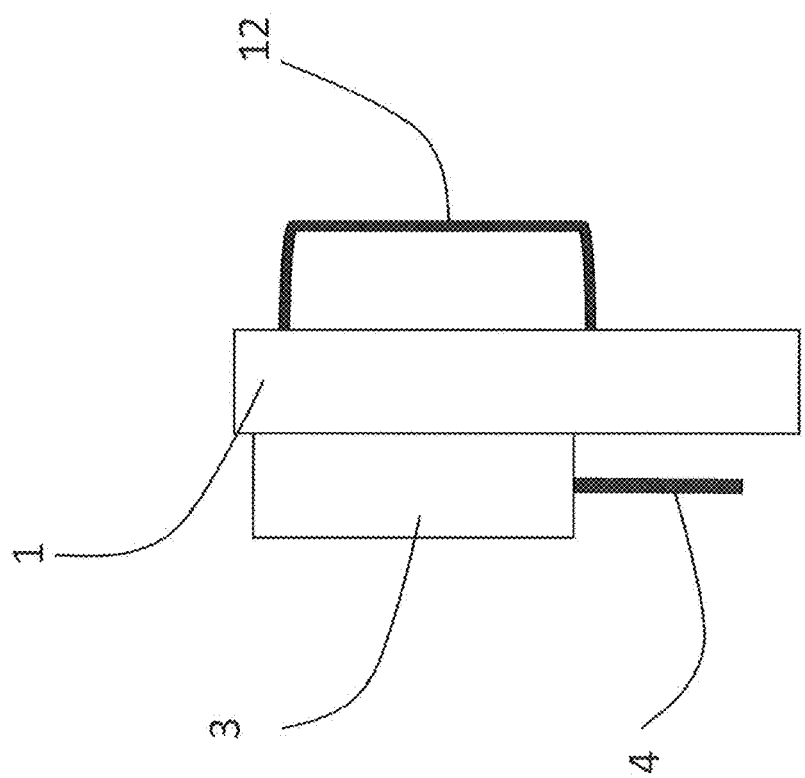
FIG. 3 depicts a side view of the system showing the belt mount.
Figure 4:
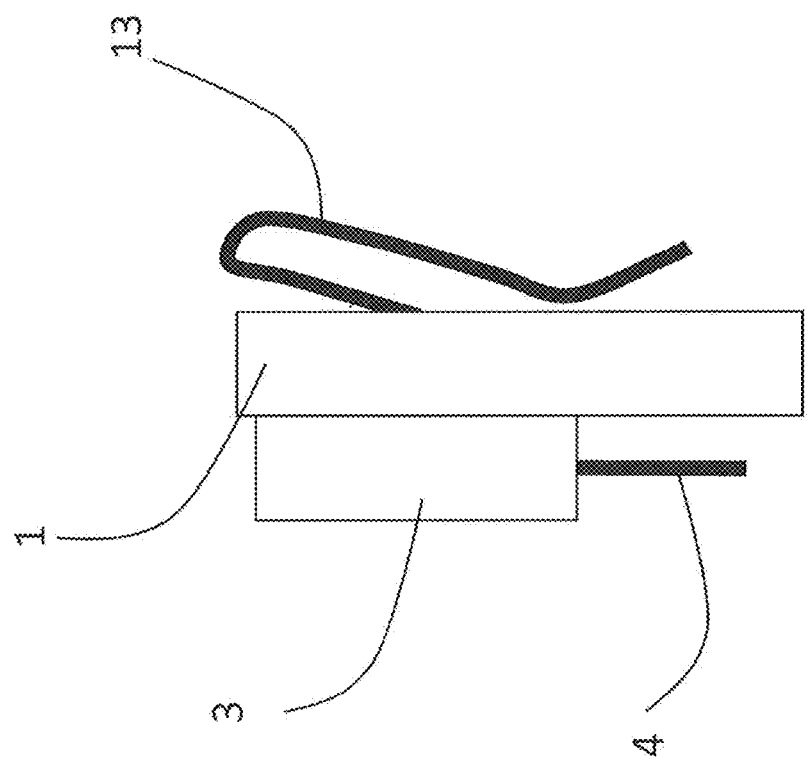
FIG. 4 depicts a side view with a hook shaped belt mount.

Another Exemplary Embodiment is illustrated in FIG. 3. In this exemplary embodiment, a belt attachment loop is attaching the mounting base 1 to a user's belt 2. FIG. 3 shows a belt mounting loop 12 that can easily mount mounting base 1 to a user's belt 2. Alternatively, the PHPS can also contain a belt 2 as part of the mounting base 1 as a single unit.

Exemplary Embodiment 4 represents another mounting configuration, in which a belt clip 13 is used to mount the mounting base 1 of the PHPS on a belt 2.

Figure 5:
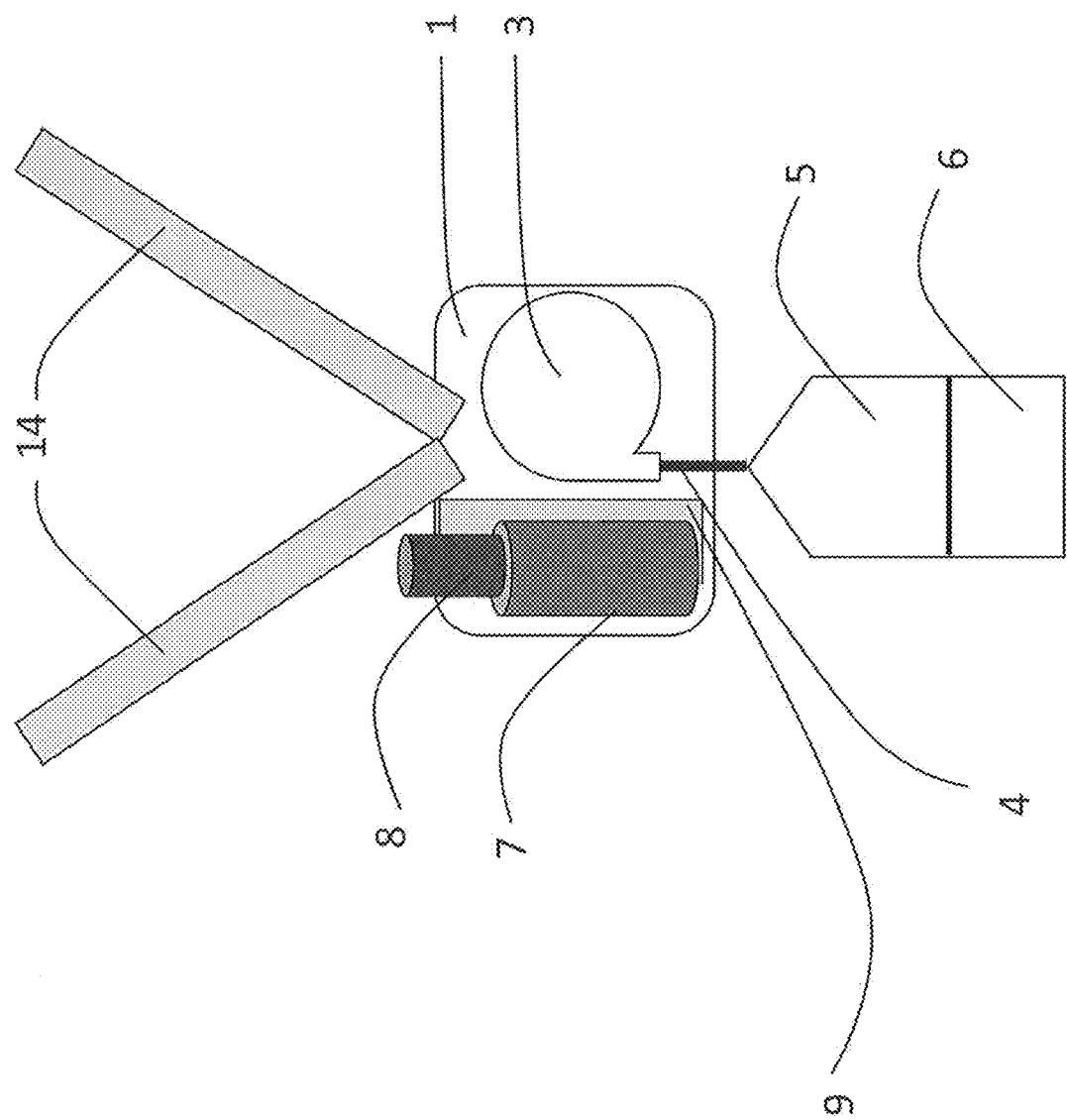
FIG. 5 depicts the primary system mounted on a lanyard.

FIG. 5 represents another Exemplary Embodiment. This embodiment illustrates a different mounting configuration. Specifically, this configuration uses a lanyard 14 as an approach for someone that does not have a belt 2 or does not wish to wear the system around their waist. This exemplary embodiment can be used to attach to a purse, briefcase, backpack or worn around the user's neck or wrist.

Figure 6:
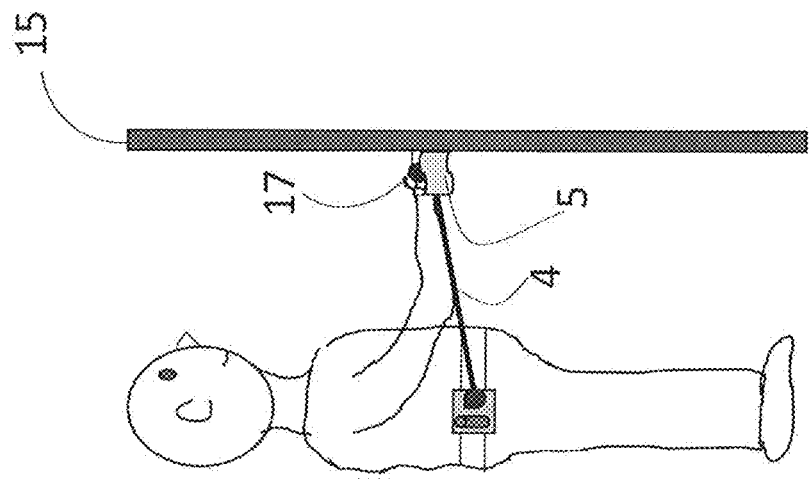
FIG. 6 depicts an individual approaching a door.
Figure 7:
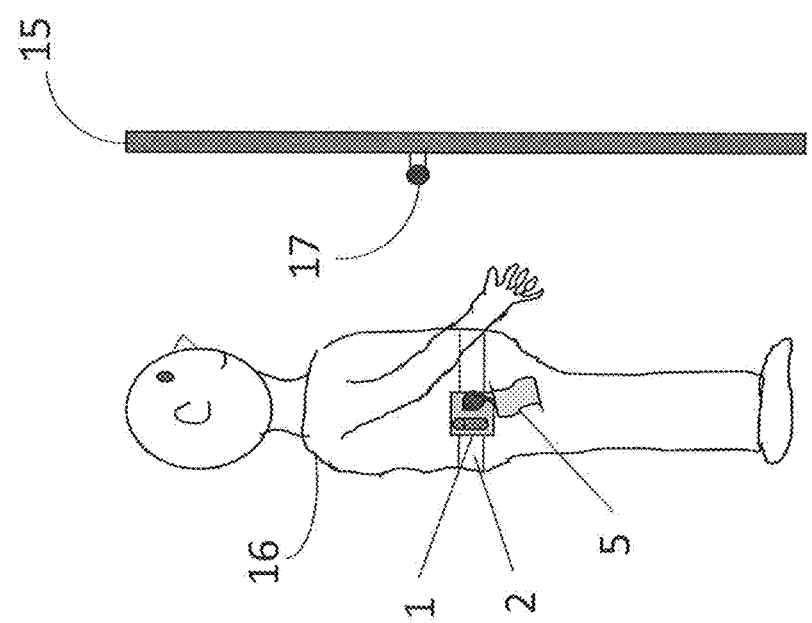
FIG. 7 an individual using the PUPS to open the door.

FIG. 6 represents an embodiment of the invention worn by a user 16 who is standing in front of a door 15. In FIG. 7, the user 16 is shown with his hand in the mitt-like cloth with the retractable cord 4 extended. As illustrated, the user 16 is gripping the door handle 17, without contact of his hand with the door handle 17. The PIPS of the current invention will greatly assist the user in keeping their hands clean to avoid the normal transmission a person is subject to when the hand is contaminated, and they subsequently touch their face, eyes or food, etc. This approach is easy, quick to use, and the combination of a quickly donning mitt and removing the mitt, along with sanitizing solution and with simple attachments that encourage unencumbered use by an individual.

Although different exemplary embodiments are disclosed, the invention is not limited thereto as other exemplary embodiments would be readily apparent to one of ordinary skill in the art. The invention is defined by the scope of the appended claims.

What is claimed is:

1. A method of mitigating the transmission of infectious threats comprising the steps of:
   providing a first contact protection cloth attached to a user by an attachment, wherein the first cloth is connected to the attachment through a retractable cord, wherein the first contact protection cloth has a pocket on each face of the cloth configured to receive the user's hand;
   providing a second contact protection cloth on said attachment that is removable by the user to reach items that the retractable cord is unable to reach or where the user prefers to use the second contact protection cloth instead of or in addition to the first contact protection cloth;
   wherein the user places a hand into one of the pockets and pulls said first contact protection cloth on said retractable cord and places said first contact protection cloth on a publicly touched surface;
   wherein the user's hand is protected by the first contact protection cloth from infectious disease threats on the publicly touched surface; and
   providing a sanitizing bottle located on said attachment to the user, the sanitizing bottle being configured to apply sanitizing solution to the first and second contact protection cloths, the user's hand and the publicly touched surface; and
   the sanitizing bottle has a sprayer configured to spray the first and second contact protection cloths, the user's hand and the publicly touched surface, wherein the user sprays the publicly touched surface in order to clean the publicly touched surface after placing the first contact protection cloth on the publicly touched surface.

2. The method of claim 1, wherein the attachment to a person is through a belt.

3. The method of claim 1, wherein the attachment to a person is through a belt attachment loop.

4. The method of claim 1, wherein the attachment to a person is through a lanyard.

5. The method of claim 1, wherein the contact protection cloth is removable for replacement or cleaning.

* * * * *